(12) United States Patent (10) Patent No.: US 9,198,994 B2
Suissa et al. (45) Date of Patent: Dec. 1, 2015

(54) DEVICE AND SYSTEM FOR DIFFUSION OF A FRAGRANCE

(75) Inventors: David Suissa, Vincennes (FR); Frederic Wets, Paris (FR)

(73) Assignee: PRESENSIA (FR)

( * ) Notice: Subject to any disclaimer, the term of this patent is extended or adjusted under 35 U.S.C. 154(b) by 242 days.

(21) Appl. No.: 14/006,853

(22) PCT Filed: Mar. 21, 2012

(86) PCT No.: PCT/FR2012/050588
§ 371 (c)(1),
(2), (4) Date: Dec. 15, 2013

(87) PCT Pub. No.: WO2012/131232
PCT Pub. Date: Oct. 4, 2012

(65) Prior Publication Data
US 2014/0183762 A1 Jul. 3, 2014

(30) Foreign Application Priority Data
Mar. 22, 2011 (FR) ...................................... 11 52360

(51) Int. Cl.
*B01F 3/04* (2006.01)
*A61L 9/12* (2006.01)

(52) U.S. Cl.
CPC . *A61L 9/12* (2013.01); *A61L 9/122* (2013.01); *B01F 3/04085* (2013.01); *A61L 2209/11* (2013.01); *A61L 2209/111* (2013.01); *A61L 2209/133* (2013.01)

(58) Field of Classification Search
CPC ..... B01F 3/04; B01F 3/04007; B01F 3/04085
USPC .............................. 261/30, DIG. 88; 422/124
See application file for complete search history.

(56) References Cited

U.S. PATENT DOCUMENTS

| 3,795,438 | A | 3/1974 | Westenholz et al. |
| 4,059,422 | A | 11/1977 | Steiner |
| 6,481,639 | B1 | 11/2002 | Pozzo |
| 2005/0082695 | A1 | 4/2005 | Scholz |
| 2006/0219962 | A1 | 10/2006 | Dancs et al. |
| 2008/0193328 | A1 | 8/2008 | Crapser et al. |
| 2009/0151447 | A1 | 6/2009 | Jin et al. |
| 2010/0090022 | A1* | 4/2010 | Hayashida ...................... 239/99 |

FOREIGN PATENT DOCUMENTS

FR 2620622 A1 3/1989
FR 2877845 A1 5/2006

OTHER PUBLICATIONS

International Search Report issued Jun. 22, 2012 re: PCT/FR2012/050588.

* cited by examiner

*Primary Examiner* — Robert A Hopkins
(74) *Attorney, Agent, or Firm* — Cantor Colburn LLP (57) ABSTRACT

A compact fragrance diffuser 1 including a ventilation corridor, an air flow generator, a fixing support on the downstream side of the air flow generator and adapted to fix a fragrance cartridge there, a partition in the ventilation corridor between the air flow generator and the fixing support, the state of which can be modified between at least a partitioning state and a non-partitioning state, and a servocontrol system between the air flow generator and the partition such that the partition is in the partitioning state if the air flow generator is stopped, the partition and the ventilation corridor being produced at least in part in a material inert to the fragrances.

17 Claims, 3 Drawing Sheets

DEVICE AND SYSTEM FOR DIFFUSION OF A FRAGRANCE

TECHNICAL FIELD

The invention is generally concerned with the field of fragrance diffusion.

The invention is more particularly concerned with a compact fragrance diffuser.

Here 'compact diffuser' means a light diffuser of small overall size so that it can be held in one hand. For example, the present compact diffuser may be moved easily by a single user from one room to another of an apartment to be scented or from one place in a room to another place in the same room. The compactness of the present diffuser notably distinguishes it from heavy and bulky diffusers sometimes installed as an integral part of the building or the furniture.

BACKGROUND

Various compact fragrance diffusers are known in the art.

These compact diffusers most often comprise a reservoir for substances in the liquid state evaporated by atomization of the liquid via a nozzle by means of the Venturi effect. In some sophisticated diffusers, evaporation is facilitated by the application of acoustic vibrations at high frequencies, the effect of which is to reduce the size of the vapor droplets and therefore to increase the area of the liquid in contact with the air and thus improve the diffusion of the fragrance.

In some other diffusers, the fragrance molecules are incorporated beforehand into solid supports, for example polymers. The substances are diffused into the air by heating these solid supports and/or by means of a flow of air over the surface of these solid supports, which techniques have the effect of progressively detaching the fragrance molecules from the solid supports and diffusing them into the surrounding air.

In the field of fragrance diffusion, a distinction is drawn between diffusers adapted to diffuse a single fragrance and diffusers adapted to diffuse a plurality of different fragrances. The expressions single-fragrance and multi-fragrance diffusers are used.

Multi-fragrance diffusers are most often designed to diffuse only one fragrance at a time. The selection of the fragrance to be diffused is the result of a choice made by the user or is controlled by electronic data processing or audiovisual means in the context of multi-sensorial multimedia works. These multi-fragrance diffusers are relatively complex to design and relatively costly.

Multi-fragrance diffusers come up against the difficulty of avoiding cross-fragrance pollution caused by migration of olfactory molecules between the different fragrance reservoirs or contamination or impregnation of components of the diffuser by the different olfactory molecules. The problem arises from the fact that any fragrance, even a dry fragrance, i.e. one integrated onto a solid support, is made up of molecules that coat or impregnate the materials that constitute the diffuser. These materials may then be qualified as reactive to the fragrances; this is the case with most plastics, for example. Now, it is known that mixing a plurality of fragrances is incompatible with the required subtlety of the odors.

By impregnating the components of a diffuser with fragrance molecules is meant here the action whereby fragrance molecules that come into contact with said components penetrate them and diffuse into them.

The document FR02620622A1 proposes a solution to the problem of cross-fragrance pollution in a multi-fragrance diffuser. That document describes a cartridge structured as a plurality of absorbent areas that are soaked in a liquid, the areas being separated from one another by non-adsorbent elements to prevent the migration of different fragrance molecules between areas. The above document does not discuss pollution between the soaked areas and the rest of the diffuser.

In the case of single-fragrance diffusers, migration of fragrance molecules to or impregnation of fragrance molecules into the components of the diffuser does not cause any cross-fragrance pollution problem if they always diffuse the same fragrance, which is the most frequent situation. Once empty, the diffuser is either thrown away or refilled with the same liquid or solid supports impregnated with the same substance.

The cross-fragrance pollution problem arises in the case of single-fragrance diffusers designed to diffuse sequentially a plurality of different fragrances, chosen by the user, because the olfactory molecules of a first fragrance migrate from the liquid reservoir or the impregnated solid supports to the various components of the diffuser and coat them. Consequently, when the user substitutes a second fragrance for a first fragrance, the second fragrance will be polluted by the residue of the first fragrance.

A solution to this problem is described in the document EP1054697 in which the volatile substance is contained in a reservoir one face of which is of spherical shape to enable it to be isolated by rotating the reservoir when odor diffusion is not required. This diffuser has the following drawbacks: the size of the diffuser is necessarily large in relation to that of the active olfactory part because the latter is contained in a small part of a cylindrical channel in an element of orbicular shape; the orbicular shape and the sealing effect of the spherical surface are relatively complex to produce. In the final analysis, the diffuser described in the above document is very complex, relatively bulky and relatively costly.

Also known is a single-fragrance diffuser developed by the company ScentAir and marketed under the trade name Scent-Wave®. This diffuser comprises a ventilation corridor, a fan and a fragrance reservoir. The fans equipping this type of diffuser are generally cheap fans with plastic material blades that easily become coated with fragrance molecules. For what it's worth, the problem of pollution between fragrances diffused consecutively does not arise in this diffuser because the ventilation corridor, the fan and the fragrance reservoir are fastened together and form an assembly, one assembly being substituted for another to change the fragrance to be diffused or to refill the diffuser with fragrance. Clearly said assembly constitutes a refill that is complex to design and relatively costly.

BRIEF SUMMARY

In this context, the present invention proposes a compact fragrance diffuser enabling one or more of the drawbacks referred to above to be overcome. The present invention more particularly proposes a compact fragrance diffuser enabling the cross-fragrance pollution problem to be overcome and that is simple to use and of low cost.

To this end, the diffuser in accordance with the invention essentially comprises:
 a ventilation corridor comprising an inlet and an outlet,
 an air flow generator adapted to propel air in the ventilation corridor so that air circulates in the upstream to downstream direction from the inlet to the outlet of the ventilation corridor, a fixing support on the downstream side of the air flow generator and adapted to fix a fragrance cartridge there so that the fragrance cartridge is on the path of the propelled air, a partition in the ventilation corridor between the air flow generator and the fixing support, the state of the partition being modifiable between at least:

a partitioning state in which the partition prevents air circulating between a first space of the ventilation corridor on the upstream side of the partition and a second space of the ventilation corridor on the downstream side of the partition, and a non-partitioning state in which the partition allows air to circulate between the first and second spaces of the ventilation corridor, and a servocontrol system between the air flow generator and the partition such that the partition is in the partitioning state when the air flow generator is stopped, the partition and the ventilation corridor being produced at least in part from a material that does not become impregnated with fragrance.

Whilst being simple to use and of low cost (not least because the air flow generator and the ventilation corridor are not disposable in the same way as the fragrance cartridge), which make it a consumer product, the diffuser advantageously makes it possible to overcome the cross-fragrance pollution problem by preventing diffusion of fragrance molecules from the fragrance cartridge into said first space of the ventilation corridor containing the air flow generator, and this is the case whether the diffuser is operating or not.

In accordance with one feature of the invention, the parts of the ventilation corridor and the partition made from a material inert to the fragrances are internal surfaces delimiting the second space of the ventilation corridor on the downstream side of the partition in its partitioning state.

The diffuser therefore advantageously has a low cost in that the parts made from a material that is inert to the fragrances, which materials are generally more costly than plastic, are restricted to the strict minimum.

In accordance with another feature of the invention, the diffuser further comprises a sensor adapted to detect at least that the partition is leaving the partitioning state, the servocontrol system comprising control electronics adapted to start the air flow generator when the sensor detects that the partition is leaving the partitioning state.

The diffuser therefore advantageously provides for automatic starting of the air flow generator as soon as the partition is no longer in its partitioning state.

The sensor is moreover adapted to detect the partition reaching the partitioning state, the control electronics being further adapted to stop the air flow generator when the sensor detects the partition reaching the partitioning state.

The simplicity and user friendliness of the diffuser are therefore advantageously increased and the air flow generator being left operating to no purpose when the partition is in its partitioning state is automatically prevented.

In accordance with another feature of the invention, the diffuser comprises a switch adapted to start and stop the air flow generator, the servocontrol system comprising control electronics adapted to modify the state of the partition so that:

the partition leaves the partitioning state after the air flow generator has been started, and the partition reaches the partitioning state before the air flow generator is stopped.

The diffuser therefore advantageously provides for more refined management of the operation of the diffuser in the sense that diffusion of fragrance into the first space containing the air flow generator is prevented whether the air flow generator is operating, stopped or in a transient state.

In accordance with a first embodiment of the invention, the partition comprises a panel adapted to cooperate with a slot crossing the ventilation corridor so that the panel slides in the slot.

Thus the diffuser provides an advantageous embodiment including a partition of simple and low-cost design.

In accordance with a first variant of the first embodiment of the invention, the sliding of the panel in the slot is brought about by turning over the diffuser, the panel sliding under its own weight.

The diffuser therefore advantageously features a simple and low-cost arrangement of the panel with respect to the rest of the diffuser.

In accordance with a second variant of the first embodiment of the invention, the diffuser comprises a lead screw adapted to cause the panel to slide in the slot, the lead screw being driven in rotation by a motor, the panel sliding vertically from a low position corresponding to the partitioning state to a high position corresponding to the non-partitioning state, a minimal voltage at the terminals of the motor enabling retention of the panel in the high position and the assembly formed by the motor and the lead screw being adapted to allow the panel to fall if the minimal voltage drops below a certain threshold.

The diffuser therefore advantageously provides for the panel to fall back into its partitioning state in the event of a failure of the power supply to the air flow generator or in a low power situation.

In accordance with a second embodiment of the invention, the partition comprises a diaphragm.

The diffuser therefore advantageously makes it possible to vary the flow rate of the air reaching the fragrance cartridge.

In accordance with a third embodiment of the invention, the partition comprises a slatted blind comprising a plurality of slats. Each slat is mounted to be mobile in rotation about a horizontal axis so as to be raised by the force of the air propelled by the air flow generator and to fall when the air flow generator stops.

The diffuser therefore advantageously makes it possible to slave the modification of the partitioning state of the partition to the operation of the air flow generator entirely mechanically and more particularly without requiring any control electronics.

In accordance with another feature of the invention, the diffuser comprises a second partition on the downstream side of the fixing support.

The diffuser therefore advantageously makes it possible entirely to prevent natural diffusion of fragrance molecules even if the air flow generator is not used.

In accordance with another feature of the invention, the diffuser comprises means for inserting and withdrawing at least one cartridge into/from the ventilation corridor at the level of the fixing support.

In accordance with another feature of the invention, the air flow generator comprises a turbine generating a pressure rise between 25 and 200 pascals in the air passing through the cartridge.

In accordance with another feature of the invention, the diffuser takes the general form of a parallelepiped:
  less than 20 cm wide, preferably 5.3 cm wide,
  more than 2 cm and less than 20 cm deep, preferably less than 5 cm deep, and
  less than 20 cm high, preferably 11.5 cm high.

In accordance with another feature of the invention, the diffuser further comprises a device for detecting absence of the cartridge in the ventilation corridor, this device in conjunction with the control electronics enabling starting of the air flow generator if at least one cartridge is absent in the ventilation corridor to be prevented.

In accordance with another feature of the invention, the diffuser further comprises a light source and a luminous intensity sensor on respective opposite sides of the fixing support adapted to sense a state of depletion of the cartridge and to alert the user thereto.

The invention also concerns a fragrance diffusion system comprising a fragrance diffuser in accordance with the invention and a fragrance cartridge adapted to be fixed into the fixing support.

The system therefore advantageously has a low cost, not least because the air flow generator and the ventilation corridor are not disposable in the same way as the fragrance cartridge, the latter being the only component of the system that has to be replaced to change the fragrance to be diffused or to refill the diffuser with fragrance.

BRIEF DESCRIPTION OF THE DRAWINGS

Other features and advantages of the invention will emerge clearly from the following description thereof given by way of nonlimiting example and with reference to the appended drawings, in which.

DETAILED DESCRIPTION

Figure 1:
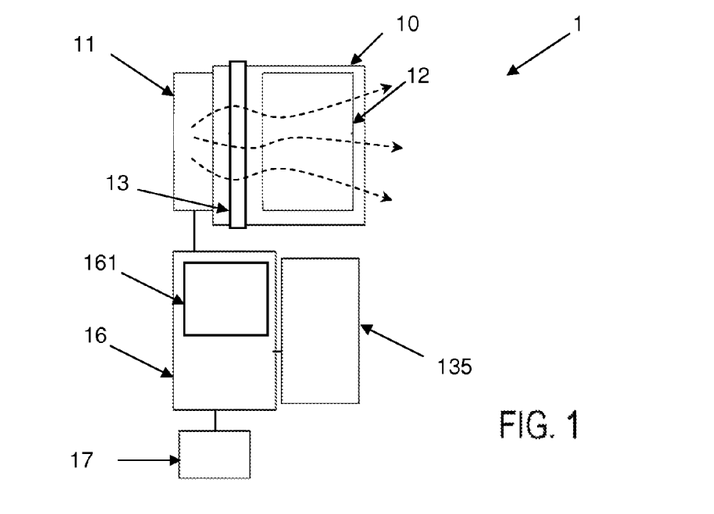
FIG. 1 represents diagrammatically the diffuser in accordance with the invention.

As shown in FIG. 1, the compact fragrance diffuser 1 comprises:
 a ventilation corridor 10,
 an air flow generator 11,
 a fixing support 12,
 a partition 13,
 a servocontrol system 16 between the air flow generator and the partition.

These components of the diffuser may be arranged in a casing.

The ventilation corridor 10 comprises an inlet 101 and an outlet 102. It is open to the exterior environment at its inlet and at its outlet. Its function is to guide air between its inlet and its outlet in a defined ventilation direction. Its section in a plane perpendicular to the ventilation direction may rectangular, circular, etc. The ventilation corridor may be formed by a portion of the casing.

The air flow generator 11 is adapted to propel air in the ventilation corridor. To be more specific, the air flow generator may be:

attached, for example by a clip, at the inlet of the ventilation corridor,
placed in the ventilation corridor, or
held by a first holding member of the casing,
its function being to propel air from the exterior environment so that air circulates in the upstream to downstream direction from the inlet of the ventilation corridor to its outlet.

The air flow generator 11 comprises a fan, for example. A cheap fan is preferred in order to minimize the cost of the diffuser. However, this type of fan often comprises plastic blades of mediocre quality, notably extremely porous and open to attack by the fragrance in the sense that it is easily impregnated by the fragrance molecules that reach it. The air flow generator also comprises an electrical power supply, for example a battery, or a mechanical power supply, for example a spring wound by hand.

The fixing support 12 is on the downstream side of the air flow generator and adapted to fix a fragrance cartridge 2 thereto so that the fragrance cartridge is on the path of the propelled air. To be more specific, the fixing support may be:
 attached, for example by a clip, at the outlet of the ventilation corridor,
 placed in the ventilation corridor, or
 held by a second holding member of the casing.

By fragrance cartridge 2 is meant a part that allows air to pass through or around it. The fragrance cartridge contains fragrance so that fragrance molecules are carried away by the air passing through or around the cartridge. The dimensions of the fragrance cartridge are proportionate to the dimensions of the ventilation corridor. In accordance with a first example shown in FIGS. 2*a* and 2*b*, the dimensions of the exterior perimeter of the cartridge are equal to those of the interior perimeter of the ventilation corridor so that the cartridge can be inserted therein and allow air to pass through it. In accordance with a second example shown in FIG. 5, the dimensions of the exterior perimeter of the cartridge are less than the dimensions of the interior perimeter of the ventilation corridor so that the cartridge occupies only a portion of the section of the ventilation corridor and allows air to pass around the cartridge.

The partition 13 is situated in the ventilation corridor 10 between the air flow generator 11 and the fixing support 12. The state of the partition is modifiable between at least:
 a partitioning state in which the partition prevents air from circulating between a first space 14 of the ventilation corridor on the upstream side of the partition and a second space 15 of the ventilation corridor on the downstream side of the partition, and
 a non-partitioning state in which the partition allows air to circulate between the first and second spaces of the ventilation corridor.

The partition is made from a material impermeable to air.

In the partitioning state, the partition prevents air from circulating. The junction between the partition and the ventilation corridor is not necessarily totally hermetically sealed. A clearance between the partition and the ventilation corridor that is typically less than 2 mm is allowed.

The section of the corridor may be constant or vary. The section of the ventilation corridor on the upstream side of the partition is smaller than the section of the ventilation corridor on the downstream side of the partition, for example.

The dimensions of the surface of the partition are proportionate to the dimensions of the section of the ventilation corridor, and more particularly to the dimensions of the section of the ventilation corridor on the upstream side of the partition. In one embodiment of the invention, the surface of the partition is larger than the section of the ventilation corridor in respect of at least one of their dimensions, the partition dividing the ventilation corridor into two parts and holding members (not shown) being arranged between said two parts of the ventilation corridor to hold the partition at least in its partitioning state. In another embodiment of the invention, the surface of the partition is slightly smaller than the section of the ventilation corridor in respect of at least one of their dimensions, a difference less than 2 mm in respect of at least one dimension typically being allowed and a portion of the interior perimeter of the ventilation corridor having this dimension serves as an abutment to hold the partition at least in its partitioning state.

Thus air laden with fragrance molecules cannot flow back in the first space toward the air flow generator, more particularly toward the blades of the fan or any other component comprising materials liable to be impregnated with fragrance.

By a servocontrol system is meant an automatic system the operation of which is governed by the difference between actual behavior and required behavior. The servocontrol system 16 between the air flow generator and the partition is such that the partition is in the partitioning state when the air flow generator is stopped. The servocontrol system on the one hand guarantees correct operation of the diffuser and on the other hand simplifies use of the diffuser by automating it.

The partition and the ventilation corridor are made at least in part from a material inert to the fragrances. By a material inert to the fragrances is meant a material with which the fragrance molecules do not interact and which therefore cannot be impregnated with or contaminated by the fragrance. Said material inert to the fragrances may be aluminum, a metal such as copper or zinc, glass or a material surface-treated to prevent fragrance molecules impregnating it (this list is not limiting on the invention).

In accordance with a preferred embodiment of the invention, the parts of the ventilation corridor and the partition made from a material inert to the fragrances comprise internal surfaces delimiting the second space 15 of the ventilation corridor on the downstream side of the partition in its partitioning state. Thus only the face of the partition facing toward the fixing support and the interior perimeter of the part of the ventilation corridor on the downstream side of the partition are made from a material inert to the fragrances. The cost of the diffuser in accordance with this embodiment of the invention is reduced relative to the cost of a diffuser made entirely from a material inert to the fragrances, materials inert to the fragrances being more costly than the materials sensitive to the fragrances generally used in the field of the invention, such as plastics.

The fragrance diffuser 1 therefore has a number of advantages.

Firstly, it can advantageously solve the cross-fragrance pollution problem by preventing the diffusion of olfactory molecules from the fragrance cartridge 2 into said first space 14 of the ventilation corridor in which the air flow generator is situated, whether the diffuser is operating or stopped; when operating, the fan creates a flow of air that opposes diffusion of the olfactory molecules in said first space and when it is stopped the partition prevents diffusion of the olfactory molecules in said first space.

Secondly, it is simple to use because it is automated, which avoids the user having to manipulate the diffuser and solves the cost-fragrance pollution problem, this problem advantageously becoming transparent for the user.

Thirdly, it is of low cost. In fact, on the one hand it does not necessitate an air flow generator comprising a fan with blades made from a material inert to the fragrances, which would be costly, and on the other hand, in contrast to the ScentWave® product described in the introduction, the fan and the ventilation corridor are not disposable in the same way as the fragrance cartridge, which constitutes the only component of the diffuser in accordance with the invention that has to be substituted for another to change the fragrance to be diffused or to refill the diffuser with fragrance.

These advantages advantageously make the fragrance diffuser in accordance with the invention a consumer product.

Figure 2A:
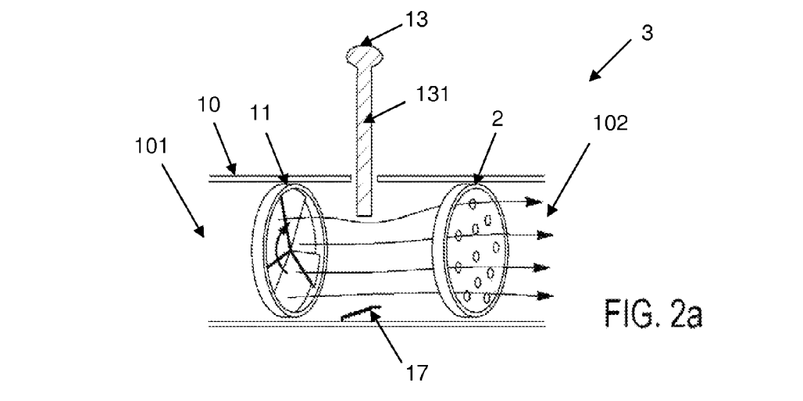
FIGS. 2*a* and 2*b* represent the system in accordance with the invention in the first embodiment of the diffuser in accordance with the invention.
Figure 2B:
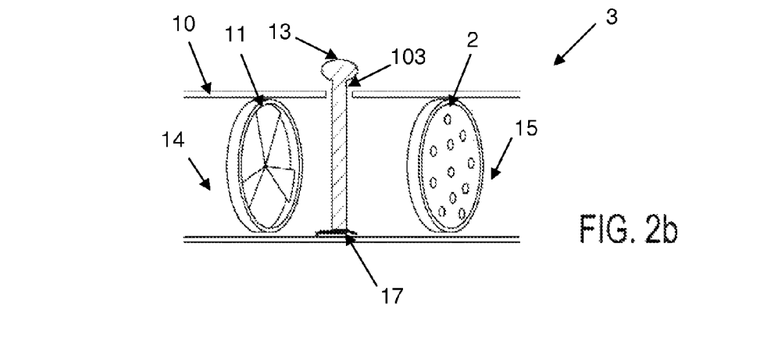

In accordance with a first embodiment of the diffuser, notably shown in FIGS. 2a and 2b, the partition 13 comprises a panel 131 adapted to cooperate with a slot 103 formed across the ventilation corridor so that the panel slides in the slot. The slot is preferably perpendicular to the average direction of circulation of air in the ventilation corridor. The panel is therefore itself also perpendicular to the average direction of circulation of air in the ventilation corridor. However, a difference of a few degrees, or even a few tens of degrees, relative to this perpendicular relationship can be envisaged without departing from the scope of the invention as claimed.

In this first embodiment of the invention, the partition is advantageously of simple and low-cost design. The partition may equally be removable from the corridor, even from the casing, and include a holding member enabling the user to withdraw it or insert it by sliding it in the slot. The partition can therefore advantageously be changed for a new partition and/or easily cleaned, for example with alcohol, to remove any fragrance molecules retained on its surface inert to the fragrances that is exposed to the fragrance cartridge.

In accordance with one feature of the invention, the diffuser further comprises a sensor 17 adapted to detect at least that the partition is leaving the partitioning state. The servocontrol system comprises control electronics 161 adapted to start the air flow generator when the sensor detects that the partition is leaving the partitioning state. The sensor is a switch, for example.

The diffuser therefore advantageously provides for automatic starting of the air flow generator as soon as the partition is no longer in its partitioning state.

In accordance with another feature of the invention, the sensor is further adapted to detect that the partition is reaching the partitioning state. The control electronics are then further adapted to stop the air flow generator when the sensor detects that the partition is reaching the partitioning state.

The diffuser is therefore advantageously easier and more user friendly to use and automatically prevents the air flow generator from being left in operation when the partition is in its partitioning state. The diffuser in accordance with the invention is therefore advantageously portable in the sense that it does not need to be connected to the electrical mains power supply, its energy requirements being low and as economical as possible.

For example, in the first embodiment of the diffuser in accordance with the invention, when the user removes the partition, the sensor detects this and the fan is started automatically, and when the user inserts the partition, the sensor detects this and the fan is stopped automatically.

In accordance with a variant of the first embodiment of the diffuser, the sliding of the panel in the slot is brought about by turning the diffuser over. The panel then slides under its own weight. An abutment in the casing enables retention of the partition so that turning the diffuser over again returns it to its partitioning state. For example, when the user turns the diffuser over, the partition slides into its non-partitioning state, the sensor detects this and the fan is started automatically, and, when the user turns the diffuser over again, the partition slides into its partitioning state, the sensor detects this and the fan is automatically stopped. In accordance with this variant, the sensor may equally well be a switch, as envisaged above, or a gyroscopic sensor.

Figure 5:
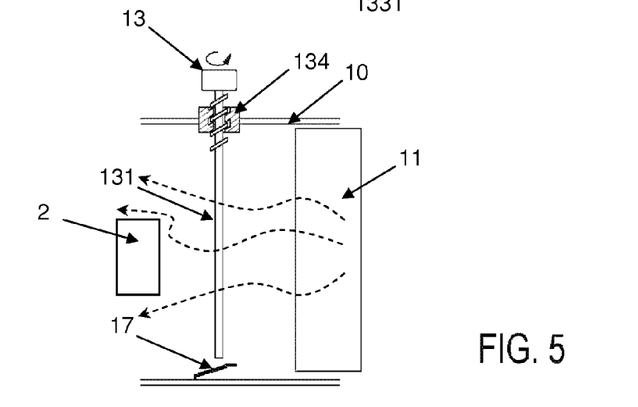
FIG. 5 represents a portion of the diffuser in accordance with a variant of its first embodiment.

In accordance with another variant of the first embodiment of the diffuser that is represented in FIG. 5, the latter comprises a lead screw 134 adapted to cause the panel to slide in the slot. The lead screw is driven in rotation by a motor 135, for example a low-voltage motor. The panel slides vertically from a low position corresponding to the partitioning state to a high position corresponding to the non-partitioning state. Maintaining a minimal voltage at the terminals of the motor enables retention of the panel in the high position. The assembly formed of the motor and the lead screw is adapted to allow the panel to fall if the voltage drops below a certain threshold.

The power supply of the motor is advantageously the same as that of the air flow generator.

The diffuser in accordance with this other variant of the first embodiment of the invention therefore advantageously provides for the panel to drop into its partitioning state in the event of failure of the power supply of the air flow generator. The parts of the diffuser on the upstream side of the partition are therefore protected from pollution by the olfactory molecules even in the event of a failure of the power supply of the diffuser.

In accordance with another feature of the invention, the diffuser does not comprise a sensor but does comprise a switch adapted to start and stop the air flow generator. The servocontrol system then comprises control electronics adapted to modify the state of the partition. For example, the air flow generator is started via the switch, after which the control electronics modify the state of the partition from its partitioning state to its non-partitioning state; or, conversely, the control electronics modify the state of the partition from its non-partitioning state to its partitioning state before the air flow generator is stopped.

The diffuser therefore advantageously enables automatic placement of the partition in its non-partitioning state as soon as the air flow generator is started and automatic placement of the partition in its partitioning state as soon as the air flow generator is stopped. More refined management of the operation of the diffuser is achieved in the sense that the diffusion of fragrance in the first space containing the air flow generator is prevented whether the air flow generator is operating, stopped or in a transient state. Here by a transient state of the air flow generator is meant the period of operation during which the fan is switched on but has not yet reached its operating rotation speed or the period of operation during which the fan is switched off but the blades are still turning, before they stop completely.

Figure 3:
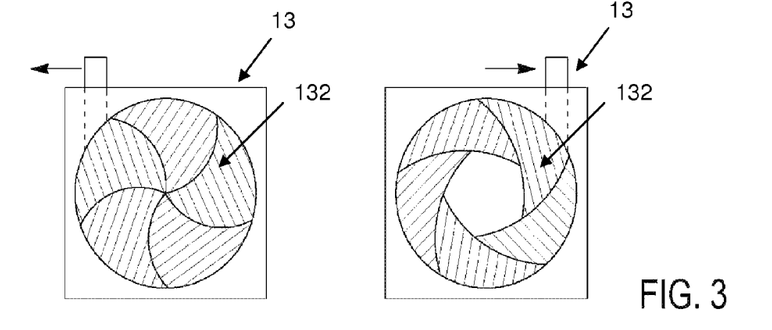
FIG. 3 represents the partition in accordance with the second embodiment of the diffuser in accordance with the invention.

In a second embodiment of the invention, the partition comprises a diaphragm 132 as shown in FIG. 3. The diaphragm is more particularly an iris diaphragm enabling continuous modification of the state of the partition between its partitioning state and its non-partitioning state. The diffuser therefore advantageously enables variation of the flow rate of the air reaching the fragrance cartridge. The user is therefore advantageously able to vary the diffusing power of the diffuser, for example as a function of the volume of the room into which it diffuses or to economize on fragrance.

The diffuser in accordance with the second embodiment of the invention may also comprise:
- a sensor 17 adapted to detect at least that the diaphragm is leaving or reaching the partitioning state, the servocontrol system comprising control electronics 161 adapted to start the air flow generator when the sensor detects that the diaphragm is leaving or reaching the partitioning state, or
- a switch adapted to start and stop the air flow generator, the servocontrol system comprising control electronics adapted to modify the state of the diaphragm in the manner described above.

Figure 4:
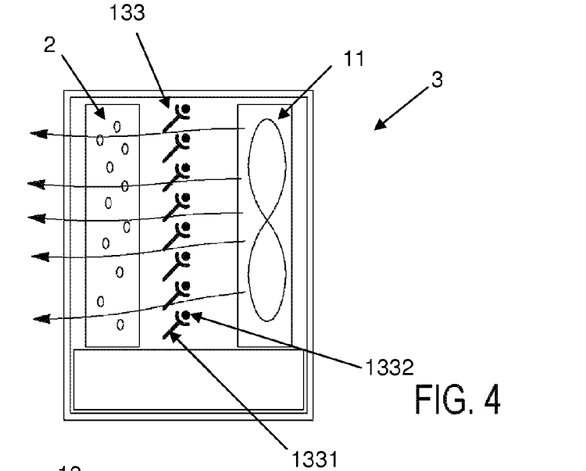
FIG. 4 represents the system in accordance with the invention in the third embodiment of the diffuser in accordance with the invention.

In a third embodiment of the invention represented in FIG. 4, the partition comprises a slatted blind 133. The slatted blind comprises one or more slats 1331. Each slat is mounted to be mobile in rotation about a horizontal axis 1332 so as to be raised by the force of the air propelled by the air flow generator and to fall when the air flow generator is stopped. In the case of a plurality of slats, each slat rests on the underlying slat when in the lowered position, the bottom slat resting on the bottom of the corridor, so that the lowered slats constitute the partition in the partitioning state.

The diffuser therefore advantageously enables modification of the partitioning state of the partition to be slaved to the operation of the air flow generator entirely mechanically. Servocontrol is effected exclusively by the force of the air propelled by the fan. To be more specific, the third embodiment of the diffuser requires neither control electronics nor a sensor, requiring only a switch for starting or stopping the fan.

In accordance with another feature of any embodiment of the diffuser, the latter comprises a second partition on the downstream side of the fixing support.

The state of the second partition is modifiable between at least:
- a partitioning state in which the second partition prevents air from circulating between the second space 15 of the ventilation corridor on the downstream side of the partition and the exterior environment, and
- a non-partitioning state in which the partition allows air to circulate between the second space 15 of the ventilation corridor and the exterior environment.

The diffuser therefore advantageously enables prevention of residual diffusion of fragrance molecules out of the diffuser when the diffuser is stopped.

The state of the second partition may be modified manually. If the fixing support is placed in the ventilation corridor, the second partition may be removably attached, for example by a clip, to the outlet of the ventilation corridor. It then functions in the manner of a simple camera lens shutter. As in this illustrative example, it is the responsibility of the user to remove it before starting the fan, because it is necessary to avoid the situation in which the fan operates with the first partition 13 in the non-partitioning position and the second partition in the partitioning position. This situation would in fact lead to discharging of air laden with olfactory molecules toward the first space 14 of the ventilation corridor on the upstream side of the first partition.

It is possible to guarantee non-occurrence of this situation automatically if the modification of the state of the second partition is likewise slaved to the operation of the air flow generator or directly to the modification of the state of the first partition 13.

The second partition or the face of the second partition facing toward the fixing support is made from a material inert to the fragrances.

It is to be noted that the fragrance cartridge is inherently disposable and replaced after use. To this end, the fragrance diffuser 1 comprises means (not shown) for insertion and withdrawal or ejection of a cartridge into/from the ventilation corridor 10 at the level of the fixing support 12. These insertion and withdrawal means are optionally arranged conjointly with the fixing support 12. For example, they may comprise a so-called "push-to-open" mechanism operating like mechanisms in cameras for inserting and ejecting memory cards: the cartridge is inserted into the diffuser and pressed in to lock the mechanism, after which it is pressed in again to unlock the mechanism and enable removal of the cartridge. In another example, the insertion and withdrawal means comprise a vertical translation mechanism with a plate and a locking hook for lowering the cartridge 2 into and lifting it out of the diffuser 1, respectively, as in a toaster.

Moreover, some technical features of a plurality of other embodiments of the present compact fragrance diffuser are closely linked to the technical features of a particular fragrance cartridge to be described briefly hereinafter by way of a preamble to the description of said other embodiments of the present diffuser.

Said particular fragrance cartridge essentially comprises:
substrate elements into which a fragrance is adsorbed,
a frame,
a first grille and a second grille fixed into the frame and facing each other, each of the grilles comprising a plurality of bars.

For example, the substrate elements are spheroidal polymer material balls and the fragrance molecules are adsorbed into the entire volume of each ball.

Before adsorption of the fragrance, each of the polymer material balls has a smallest dimension equal to 3 mm and a largest dimension equal to 4 mm and after adsorption of the fragrance a smallest dimension equal to 4 mm and a largest dimension equal to 6 mm.

The flow of air through the cartridge induces an increase in the quantity of fragrance molecules diffused per unit time relative to the quantity of fragrance molecules that would be evaporated per unit time in the absence of any air flow. The desorption phenomenon is effectively conjugate with the convection effect of the flow of air.

In accordance with one feature of the cartridge, the bars of each grille are spaced from each other and the grilles are spaced from each other so that the cartridge enables retention of a single layer of substrate elements in the frame and between the grilles.

The substrate elements are therefore disposed in the cartridge in a single layer, which has a number of advantages.

Firstly, satisfactory diffusion of the fragrance molecules into the atmosphere via the flow of air necessitates a pressure lower than that which would be required if substrate elements were disposed in a plurality of layers. The constraints applying to the air flow generator 11 are commensurately lower. The typical use of fans or turbines of low or very low power and therefore of low cost and relatively quiet is advantageously sufficient and satisfactory. An increased pressure of the air passing through the cartridge of the order of 0.10 to 0.80 inches $H_2O$ at 21° C., i.e. of the order of 25 to 200 pascals, typically offers a very satisfactory result. It is to be noted that if a plurality of cartridges are juxtaposed with each other as mentioned above the power of the turbine must be increased proportionately in the aforementioned range. If only one cartridge is disposed in the diffuser, a turbine will be preferred creating a pressure rise in the air flowing through the cartridge of the order of between 25 and 50 pascals.

In accordance with another technical feature of the cartridge 2, it has a width and a length/height of the order of a few centimeters, preferably equal to 4.7 cm, and a thickness of the order of one centimeter, preferably equal to 1.4 cm.

Accordingly, the dimensions of the cartridge or its frame, which amounts to the same thing, are relatively small, which is compatible with compact diffusers 1. And, in one embodiment of the diffuser 1, the ventilation corridor 10 has a cross section of substantially greater width and length/height than the cartridge, so that the cartridge can be inserted into the ventilation corridor substantially without clearance. The ventilation corridor typically has an interior perimeter having a cross section of width and length/height equal to 4.8 cm. Accordingly, no gap is left between the frame of the cartridge 2 and the ventilation corridor 10 and all the propelled air passes through the cartridge.

One embodiment of the compact fragrance diffuser 1 takes the form of a parallelepiped:
less than 20 cm wide, preferably 5.3 cm wide,
more than 2 cm and less than 15 cm deep, and
less than 20 cm high, preferably 11.5 cm high.

In this embodiment, the ventilation corridor 10 is arranged in the depth of the diffuser so that air is aspirated from the back of the diffuser and propelled toward the front thereof. Moreover, the ventilation corridor 10 runs the entire depth of the diffuser and extends the full width of the diffuser and over a distance between one third and half the total height of the diffuser.

Moreover, the frame of the cartridge 2 may comprise at least one male fixing member on one face and at least as many female fixing members on the other face, each male member being adapted to be interengaged, preferably removably, with any of the female members. In this way, a plurality of cartridges may be joined together, their frames being juxtaposed in the direction of their thickness.

It is in the context of this option that as stated above the depth of the parallelepiped forming the diffuser may vary between 2 and 20 cm, because if, when only one cartridge is loadable into the diffuser, the latter preferably has a depth less than 5 cm, a plurality of cartridges may in fact be juxtaposed in the direction of their thickness, commensurately increasing the required depth of the diffuser. This possibility of juxtaposing the cartridges with each other remains compatible with a compact fragrance diffuser because of the small thickness of the cartridges.

Moreover, another embodiment of the diffuser comprises a device for detecting the presence or the absence of at least one cartridge in the ventilation corridor, so that this device in conjunction with the control electronics of the diffuser enables starting the air flow generator in the absence of at least one cartridge in the ventilation corridor to be prevented. For example, said device for detecting the presence or the absence of at least one cartridge in the ventilation corridor may advantageously be based on mechanical cooperation of one of the male members for clipping the cartridges together with an air flow generator power supply switch. Through contact with said male member, the introduction of a cartridge 2 into the fixing device 12 of the diffuser 1 enables application of pressure to the switch so that it goes to a position closing the power supply circuit of the air flow generator when the cartridge is completely and correctly inserted into the diffuser. This notably economizes on electrical energy by preventing operation of the diffuser if there is no cartridge in the diffuser.

Other technical features of the cartridge are advantageously exploited.

Firstly each substrate element is produced in a polymer material into which fragrance is adsorbed and which therefore has dimensions that vary in time from its initial dimensions to smaller final dimensions reached when the fragrance is entirely desorbed. The initial dimensions of the substrate elements are generally between 3 mm and 8 mm. To be more specific, the initial smallest dimension of the polymer material balls is equal to 4 mm and the initial largest dimension of the polymer material balls is equal to 6 mm, which corresponds exactly to the dimensions of the polymer material balls after adsorption of the fragrance indicated above. The final dimensions of the polymer material substrate elements 1 are between half and eight tenths of their initial dimensions.

To be more specific, the final smallest dimension of the polymer material balls is equal to 3 mm and the final largest dimension of the polymer material balls is equal to 4 mm, which corresponds exactly to the dimensions of the polymer material balls before adsorption of the fragrance indicated above.

Next, two adjacent second bars of the first grille lie within the thickness of the frame, and so a single row of a controlled number of substrate elements may be held between these two adjacent vertically disposed second bars.

The substrate elements of the row then in time becoming free to move vertically between said adjacent second bars and becoming compacted under the action of their weight, the height of the row constitutes a visual indicator of depletion of the cartridge.

Figure 6:
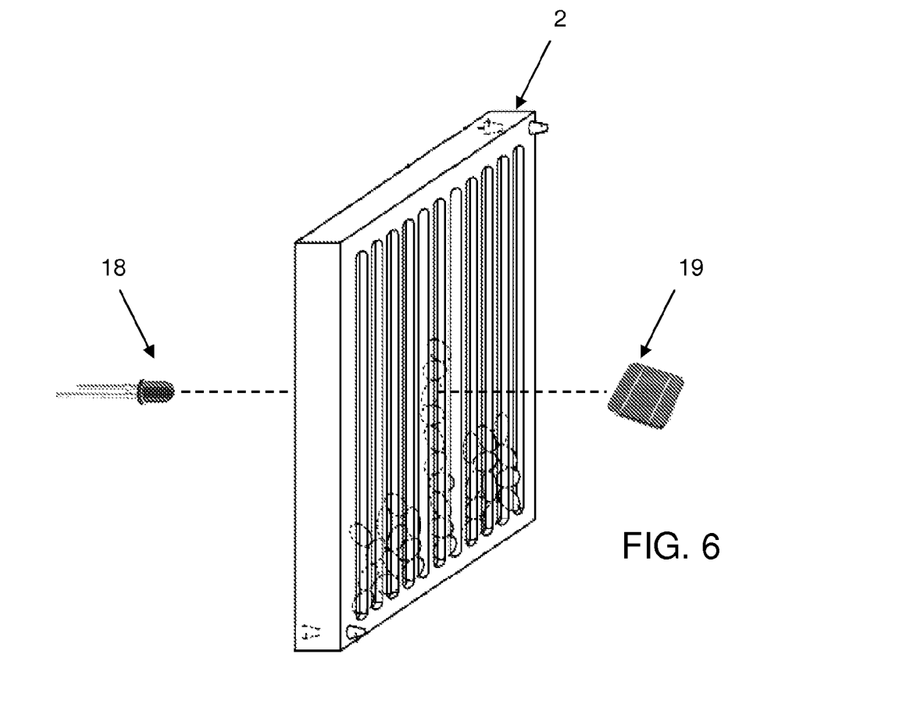
FIG. 6 shows the principle of operation of the diffuser in an embodiment adapted to warn of depletion of the cartridge.

Accordingly, a new embodiment of the diffuser 1, the principle of which is shown in FIG. 6, further comprises a light source 18, such as a light-emitting diode, and a luminous intensity sensor 19, such as a photovoltaic cell, situated on respective opposite sides of the row and at a particular height sense the height of the row falling below a threshold height and thus alert the user to depletion of the cartridge and the necessity to replace it. This alert may more particularly comprise a light signal emanating from a light-emitting diode arranged on the front of the diffuser and powered by the photovoltaic cell.

The present invention also concerns a fragrance diffusion system 3. The system comprises a fragrance diffuser 1 as described above and a fragrance cartridge 2 adapted to be fixed into the fixing support 12.

The system therefore advantageously has a low cost, not least because the air flow generator and the ventilation corridor are not disposable in the same way as the fragrance cartridge, the latter being the only component of the system that has to be replaced to change the fragrance to be diffused or to refill the diffuser with fragrance.

Before changing the fragrance to be diffused, any olfactory molecules deposited on the internal surfaces delimiting the second space 15 of the ventilation corridor on the downstream side of the partition in its partitioning state are advantageously pulled off these surfaces and dispersed into the exterior environment by starting the air flow generator if the partition or partitions are in the non-partitioning state and there is no fragrance cartridge in the fixing support.

It should be obvious to a person skilled in the art that the present invention lends itself to numerous other specific embodiments that do not depart from the field of application of the invention as claimed. Consequently, the present embodiments must be considered as illustrative and may be modified, and notably combined, within the field defined by the scope of the appended claims.

The invention claimed is:

1. A compact fragrance diffuser wherein, comprising:
a ventilation corridor comprising an inlet and an outlet,
an air flow generator adapted to propel air in the ventilation corridor so that air circulates in the upstream to downstream direction from the inlet to the outlet of the ventilation corridor,
a fixing support on the downstream side of the air flow generator and adapted to fix a fragrance cartridge there so that the fragrance cartridge is on the path of the propelled air,
a partition in the ventilation corridor between the air flow generator and the fixing support, the state of the partition being modifiable between at least:
a partitioning state in which the partition prevents air circulating between a first space of the ventilation corridor on the upstream side of the partition and a second space of the ventilation corridor on the downstream side of the partition, and
a non-partitioning state in which the partition allows air to circulate between the first and second spaces of the ventilation corridor, and
a servocontrol system between the air flow generator and the partition such that the partition is in the partitioning state when the air flow generator is stopped, the partition and the ventilation corridor being produced at least in part from a material that does not become impregnated with fragrance.

2. The diffuser as claimed in claim 1, wherein the parts of the ventilation corridor and the partition made from a material inert to the fragrances are internal surfaces delimiting the second space of the ventilation corridor on the downstream side of the partition in its partitioning state.

3. The diffuser as claimed in claim 1, further comprising a sensor adapted to detect at least that the partition is leaving the partitioning state, the servocontrol system comprising control electronics adapted to start the air flow generator when the sensor detects that the partition is leaving the partitioning state.

4. The diffuser as claimed in claim 3, wherein the sensor is further adapted to detect that the partition is reaching the partitioning state, the control electronics being further adapted to stop the air flow generator if the sensor detects that the partition is reaching the partitioning state.

5. The diffuser as claimed in claim 1, further comprising a switch adapted to start and stop the air flow generator, the servocontrol system comprising control electronics adapted to modify the state of the partition so that:
the partition leaves the partitioning state after the air flow generator has been started, and
the partition reaches the partitioning state before the air flow generator is stopped.

6. The diffuser as claimed in claim 1, wherein the partition comprises a panel adapted to cooperate with a slot crossing the ventilation corridor so that the panel slides in the slot.

7. The diffuser as claimed in claim 6, wherein the sliding of the panel in the slot is brought about by turning over the diffuser, the panel sliding under its own weight.

8. The diffuser as claimed in claim 5, further comprising a lead screw adapted to cause the panel to slide in the slot, the lead screw being driven in rotation by a motor, the panel sliding vertically from a low position corresponding to the partitioning state to a high position corresponding to the non-partitioning state, a minimal voltage at the terminals of the motor enabling retention of the panel in the high position and the assembly formed by the motor and the lead screw being adapted to allow the panel to fall if the minimal voltage drops below a certain threshold.

9. The diffuser as claimed in claim 1, wherein the partition comprises a diaphragm.

10. The diffuser as claimed in claim 1, wherein the partition comprises a slatted blind comprising a plurality of slats, each slat being mounted to be mobile in rotation about a horizontal axis so as to be raised by the force of the air propelled by the air flow generator and to fall when the air flow generator stops.

11. The diffuser as claimed in claim 1, further comprising a second partition on the downstream side of the fixing support.

12. The diffuser as claimed in claim 1, further comprising means for inserting and withdrawing at least one cartridge into/from the ventilation corridor at the level of the fixing support.

13. The diffuser as claimed in claim 1, wherein the air flow generator comprises a turbine generating a pressure rise between 25 and 200 pascals in the air passing through the cartridge.

14. The diffuser as claimed in claim 1, wherein it takes the general form of a parallelepiped:
   less than 20 cm wide,
   more than 2 cm and less than 20 cm deep, and
   less than 20 cm high.

15. The diffuser as claimed in claim 3, further comprising a device for detecting absence of the cartridge in the ventilation corridor, this device in conjunction with the control electronics enabling starting of the air flow generator if at least one cartridge is absent in the ventilation corridor to be prevented.

16. The diffuser as claimed in claim 1, further comprising a light source and a luminous intensity sensor on respective opposite sides of the fixing support adapted to sense a state of depletion of the cartridge and to alert the user thereto.

17. A fragrance diffusion system comprising a fragrance diffuser as claimed in claim 1 and a fragrance cartridge adapted to be fixed into the fixing support.

\* \* \* \* \*